(12) United States Patent
Steel et al.

(10) Patent No.: US 10,293,111 B2
(45) Date of Patent: May 21, 2019

(54) DRIVE MECHANISM FOR A DRUG DELIVERY DEVICE AND A METHOD FOR ASSEMBLING A DRUG DELIVERY DEVICE

(71) Applicant: Sanofi-Aventis Deutschland GMBH, Frankfurt am Main (DE)

(72) Inventors: Samuel Steel, Warwickshire (GB); Paul Richard Draper, Worcestershire (GB); Joseph Butler, Warwickshire (GB); David Richard Mercer, Dorset (GB)

(73) Assignee: Sanofi-Anentis Deutschland GMBH, Frankfurt am Main (DE)

( * ) Notice: Subject to any disclaimer, the term of this patent is extended or adjusted under 35 U.S.C. 154(b) by 469 days.

(21) Appl. No.: 14/913,153

(22) PCT Filed: Aug. 15, 2014

(86) PCT No.: PCT/EP2014/067471
§ 371 (c)(1),
(2) Date: Feb. 19, 2016

(87) PCT Pub. No.: WO2015/024874
PCT Pub. Date: Feb. 26, 2015

(65) Prior Publication Data
US 2016/0206822 A1    Jul. 21, 2016

(30) Foreign Application Priority Data
Aug. 22, 2013   (EP) ..................................... 13181275

(51) Int. Cl.
*A61M 5/31*    (2006.01)
*A61M 5/24*    (2006.01)
(Continued)

(52) U.S. Cl.
CPC ...... *A61M 5/31511* (2013.01); *A61M 5/2033* (2013.01); *A61M 5/24* (2013.01);
(Continued)

(58) Field of Classification Search
CPC .......... A61M 5/31511; A61M 5/31585; A61M 5/31501; A61M 5/31555; A61M 5/3146;
(Continued)

(56) References Cited

U.S. PATENT DOCUMENTS 7,553,294 B2 * 6/2009 Lazzaro ............ A61M 5/14546
604/131
9,486,586 B2 * 11/2016 Jugl ..................... A61M 5/3146
(Continued)

FOREIGN PATENT DOCUMENTS

CN         102917743         2/2013
EP         2885031 B1 *  10/2017  ......... A61M 5/3146
(Continued)

OTHER PUBLICATIONS

International Search Report and Written Opinion in International Application No. PCT/EP2014/067471, dated Jan. 1, 2015, 10 pages.
(Continued)

*Primary Examiner* — Bayan Salone
(74) *Attorney, Agent, or Firm* — Fish & Richardson P.C.

(57) ABSTRACT

The present invention concerns a drive mechanism (3) for a drug delivery device (1), which comprises a piston rod (40) comprising a first piston rod member (7) and a second piston rod member (8). The drive mechanism (3) further comprises an adjustment member (9). The drive mechanism (3) has a first state in which the first and the second piston rod member (7, 8) are moveable with respect to each other by operating the adjustment member (9), thereby adjusting the length of the piston rod (40), and wherein the adjustment member (9) is arranged at least partially inside the second piston rod member (8). Moreover, the present invention concerns a method for assembling the drug delivery device (1).

15 Claims, 5 Drawing Sheets

(51) Int. Cl.
*A61M 5/20* (2006.01)
*A61M 5/315* (2006.01)

(52) U.S. Cl.
CPC ...... *A61M 5/3146* (2013.01); *A61M 5/31555* (2013.01); *A61M 5/31585* (2013.01); *A61M 2207/00* (2013.01); *Y10T 29/49904* (2015.01)

(58) Field of Classification Search
CPC .. A61M 5/24; A61M 5/2033; A61M 5/31515; A61M 2207/00; Y10T 29/49904
See application file for complete search history.

(56) References Cited

U.S. PATENT DOCUMENTS

| | | | | |
|---|---|---|---|---|
| 2004/0158205 | A1* | 8/2004 | Savage | A61M 5/007 604/151 |
| 2009/0275914 | A1* | 11/2009 | Harms | A61M 5/24 604/506 |
| 2010/0094205 | A1* | 4/2010 | Boyd | A61M 5/31595 604/68 |
| 2010/0280461 | A1* | 11/2010 | Forstreuter | A61M 5/31515 604/228 |
| 2011/0245780 | A1* | 10/2011 | Helmer | A61M 5/31515 604/211 |
| 2012/0143146 | A1* | 6/2012 | Strehl | A61M 5/31511 604/208 |
| 2012/0283657 | A1* | 11/2012 | Kouyoumjian | A61M 5/24 604/211 |
| 2015/0209522 | A1* | 7/2015 | Jugl | A61M 5/31515 604/228 |
| 2015/0217060 | A1* | 8/2015 | Jugl | A61M 5/3146 604/228 |

FOREIGN PATENT DOCUMENTS

| | | |
|---|---|---|
| EP | 2885032 B1 * | 1/2018 |
| JP | 2013-506453 | 2/2013 |
| WO | WO2008/058665 | 5/2008 |
| WO | WO2009/132777 | 11/2009 |
| WO | WO2011/039215 | 4/2011 |
| WO | WO 2014029724 A1 * | 2/2014 ........ A61M 5/31515 |

OTHER PUBLICATIONS

International Preliminary Report on Patentability in International Application No. PCT/EP2014/067471, dated Feb. 23, 2016, 7 pages.
Rote Liste, "50. Hypophysen—, Hypothalamushormone, andere regulatorische Peptide u. ihre Hemmstoffe," Chapter 50, ed. 2008, 20 pages.

* cited by examiner

DRIVE MECHANISM FOR A DRUG DELIVERY DEVICE AND A METHOD FOR ASSEMBLING A DRUG DELIVERY DEVICE

CROSS-REFERENCE TO RELATED APPLICATIONS

This application is a U.S. national stage application under 35 U.S.C. § 371 of International Application No. PCT/EP2014/067471, filed on Aug. 15, 2014, which claims priority to European Patent Application No. 13181275.2, filed on Aug. 22,2013, the entire contents of which are incorporated herein by reference.

The present invention relates to a drive mechanism for a drug delivery device. Furthermore, the present invention concerns a method for assembling a drug delivery device.

Drug delivery devices are generally known for the administration of a medicinal product, for example insulin or heparin, but also for other medicinal products, in particular for self-administration by a patient. A drug delivery device may be configured as a pen-type injector, which may dispense a pre-set dose of a fluid medicinal product. However, the drug delivery device may also deliver a variable dose of a medicinal product.

Before the first use of the drug delivery device, the user may have to dispense a small amount of the product. Thereby, the drug delivery device may be adjusted to manufacturing tolerances of its mechanical components. The operation of dispensing a small amount of the product before the first use is also referred to as a priming operation of the drug delivery device. Users who are unfamiliar with the drug delivery device may fail or incorrectly prime their drug delivery device before dispensing the first dose. Another disadvantage of a drug delivery device requiring a priming operation is that a user might accidentally inject a priming dose. Moreover, priming operation results in a waste of a medicament as the medicament expelled during the priming operation can not be used to treat the patient.

WO 2011/039215 A1 discloses a drug delivery device which does not require a priming step.

It is an object of the present disclosure to provide a drive mechanism for use in a drug delivery device which helps to improve usability and ensures the accuracy of the first administered dose of a medicinal product.

This object is solved by the drive mechanism according to present claim 1. Further, the object is also solved by the method for assembling the drug delivery device according to the further independent claim.

According to a first aspect of the present disclosure, a drive mechanism for a drug delivery device is provided which comprises a piston rod comprising a first piston rod member and a second piston rod member. The drive mechanism further comprises an adjustment member. The drive mechanism has a first state, in which the first and the second piston rod member are moveable with respect to each other by operating the adjustment member, thereby adjusting the length of the piston rod. Further, the adjustment member is arranged at least partially inside the second piston rod member.

In particular, the drive mechanism may comprise elements corresponding structurally and functionally to the components of the dosing and drive mechanism disclosed by WO 2008/058665 A1. In particular, the drive mechanism may comprise elements corresponding structurally and functionally to the piston rod and the drive sleeve of the dosing and drive mechanism disclosed by WO 2008/058665 A1.

The first state of the drive mechanism may be a pre-assembled state. In the first state, the drive mechanism may be assembled to a cartridge holder holding a cartridge. However, in the first state, mechanical tolerances between the drive mechanism and the cartridge holder and mechanical tolerances between elements of the drive mechanism may be present. Moreover, a button may not have been assembled to the drug delivery device in the first state.

In the first state, due to manufacturing tolerances or other mechanical tolerances, the drive mechanism may be not correctly aligned to other elements of the drug delivery device. In particular, the distance between elements of the drive mechanism, for example the piston rod, and a bung of the cartridge may not be well defined. Due to mechanical tolerances and other tolerances in the manufacturing process this distance may vary from one drug delivery device to another in the first state of the drive mechanism.

In the first state, the drive mechanism is usable for preparative purposes only and is not suited for a dose setting operation or a dose dispensing operation.

The first piston rod member may be configured as a threaded insert. In particular, the first piston rod member may be configured as a threaded insert which is inserted into the second piston rod member. The second piston rod member may comprise a lead screw.

The drive mechanism may be adapted to move the bung in a distal direction further into the cartridge in a dose dispensing operation.

The terms "distal" and "proximal" shall be defined as follows. In an assembled drug delivery device, the distal end of the drive mechanism is defined as the end which is closest to a dispensing end of the drug delivery device. In an assembled drug delivery device, the proximal end of the drive mechanism is defined as the end which is furthest away from the dispensing end of the drug delivery device. Moreover, a distal direction is defined as a direction towards the distal end and a proximal direction is defined as a direction towards the proximal end.

The first piston rod member may comprise a bearing configured to abut the bung in the dose dispensing operation. The bearing may be adapted to provide a force on the bung in the dose dispensing operation such that the bung is moved forward and a medicament is expelled from the cartridge.

The adjustment member is arranged at least partially inside the second piston rod member. In particular, the adjustment member may be arranged at least partially inside the second piston rod member in the first state. The adjustment member may be adapted to be moved even further into the second piston rod member during assembly. In particular, the adjustment member may be configured to be moved into the second piston rod member to a larger extent or to be moved into the second piston rod member completely. Once the adjustment member is moved completely into the second piston rod member, the drive mechanism may be configured such that the adjustment member may not be moved relative to the second piston rod member anymore.

Therefore, the length of the piston rod may not be altered after the adjustment member has been moved completely into the second piston rod member. This ensures that, once the adjustment member has been moved completely into the second piston rod member, the first and the second piston rod member are not moveable relative to each other. Thereby, a manipulation of the adjustment member is prevented after the adjustment of the length of the piston rod has been completed. In particular, an accidental manipulation during assembly or transportation of the drug delivery device is prevented. Due to the adjustment member being arranged at least partially inside the second piston rod member a good protection against accidental damage and accidental misalignment of the drive mechanism during manufacturing or transportation may be provided.

Accordingly, arranging the adjustment member at least partially inside the second piston rod member simplifies the manufacturing process and increases the reliability of the drive mechanism.

By adjusting the length of the piston rod in the first state, tolerances of the mechanical elements are removed. Additionally, the need for a priming operation before delivering the first dose can be avoided.

The drive mechanism may further comprise a drive member, e.g. a drive sleeve. The piston rod and the drive member may be configured such that a movement of the drive member in a distal direction results in a movement of the piston rod into the distal direction. Moreover, the piston rod and the drive member may be configured such that the piston rod is not moved when the drive member is moved in the proximal direction.

The drive member and the piston rod may be threadedly engaged to each other. The engagement may be configured such that the drive member and the piston rod disengage from each other when the drive member is moved in the proximal direction.

In particular, the second piston rod member may be configured to interact with the drive member. For this purpose, the second piston rod member may comprise ratchet teeth or a lead screw.

The drive mechanism may further have a second state, in which the first piston rod member is fixed to the second piston rod member to define a fixed length piston rod. Accordingly, the second state of the drive mechanism may be defined as a state wherein the length of the piston rod is fixed. Analogously, the first state of the drive mechanism may be defined as a state wherein the length of the piston rod is variable.

In the second state the drug delivery device may be used by a patient for the application of a medicament. Accordingly, the drug delivery device may be ready to carry out a dose setting and a dose dispensing operation.

In particular, when the drive mechanism is operated for the first time in the second state, the drive mechanism can be used without the requirement of a priming step to prepare for the first dose delivery.

The adjustment member may comprise a first connection member. The first piston rod member may comprise a second connection member. The first and the second connection member may be configured to prevent a rotational movement of the adjustment member and the first piston rod member relative to each other and to permit a relative translational movement of the adjustment member and the first piston rod member when the first and the second connection member are connected to each other. In the first state, the first and the second connection member may be connected to each other. In the second state, the first and the second connection member may be connected to each other. Accordingly, in the first state and in the second state, a rotational movement of the adjustment member and the first piston rod member relative to each other may be prevented. Further, in the first state a relative translational movement of the adjustment member and the first piston rod member may be permitted. However, in the second state a relative translational movement of the adjustment member and the first piston rod member may be prevented by the interaction of other members.

In particular, the first connection member may comprise a part with a non-circular cross-section and the second connection member may comprise a non-circular opening. Accordingly, a connection of the first and the second connection member may be realized by arranging the part with the non-circular cross-section of the first connection member inside the non-circular opening. In particular, the first connection member and the second connection member may form a key and slot interface preventing any relative rotational movement between the adjustment member and the first piston rod member.

Further, the adjustment member may comprise a third connection member. The second piston rod member may comprise a fourth connection member. The third and the fourth connection member may be configured to prevent a rotational movement of the adjustment member and the second piston rod member relative to each other and to permit a relative axial movement of the adjustment member and the second piston rod member when the third and the fourth connection member are connected to each other.

In particular, when the third and the fourth connection member are connected to each other, it may still be possible to move the adjustment member into the second piston rod member such that the adjustment member is moved inside the second piston rod member either completely or at least to a larger extent than in the first state of the drive mechanism.

The first piston rod member may be moveable relative to the second piston rod member when the third and the fourth connection member are not connected to each other.

A relative movement of the first piston rod member and the second piston rod member may be prevented when the third and the fourth connection member are connected to each other. In particular, a relative rotational movement and a relative translational movement may be prevented when the third and the fourth connection member are connected to each other. Accordingly, in this case, the first and the second piston rod member may define a fixed length piston rod such that the drive mechanism is in its second state.

The third connection member and the fourth connection member may be configured to form a splined connection. For this purpose, each of the third and the fourth connection member may comprise splined elements.

The first piston rod member may comprise a fifth connection member. The second piston rod member may comprise a sixth connection member. The fifth and the sixth connection member may be connected to each other such that only a concurrent rotational and translational movement between the first and the sixth second piston rod member is permitted.

In particular, the fifth and the sixth connection member may be threads. Accordingly, a connection of the fifth and the sixth connection member may correspond to a threaded engagement of the first and the second piston rod member. In other words, when the fifth and the sixth connection member are connected to each other, an exclusive rotational and an exclusive translational movement of the first and the second piston rod member relative to each other is prevented.

The first piston rod member may be arranged at least partially inside the second piston rod member. Further, the first piston rod member may be arranged at least partially inside the adjustment member.

The adjustment member may have a contact area adapted for engagement with a tool. The tool may be used to rotate the adjustment member during an operation wherein the length of the piston rod is adjusted. The tool may be a gripping tool. Alternatively, the tool may be a shaft that is plugged into a corresponding opening of the adjustment member such that the adjustment member follows a rotation of the shaft.

The adjustment member may be arranged such that a rotational movement of the adjustment member relative to the second piston rod member advances the first piston rod member relative to the second piston rod member.

The drive mechanism may further comprise a spring member that is adapted to move the piston rod after adjustment of the length of the piston rod in a proximal direction. In particular, the spring member may be adapted to move the piston rod in the proximal direction by a short distance. Accordingly, the spring member may be a back off spring. The spring member may ensure that the piston rod is in a predefined distance to the bung after the adjustment of the length of the piston rod has been completed. The predefined distance depends on the compression length of the spring member.

The spring member may ensure that the piston rod is not in permanent abutment with the bung. For example, after a dose dispensing operation is completed, the piston rod is withdrawn from the bung by the predefined distance such that the bung may relax. Accordingly, it is prevented that fluid drips out of the cartridge after the dose dispensing operation has been completed.

Another aspect of the present invention relates to an assembly comprising the drive mechanism, a detection member and a cartridge comprising a bung, wherein the drive mechanism is adapted to move the bung in a dose dispense operation, and wherein a first piston rod member comprises a bearing configured to abut the bung in a dose dispense operation, and wherein the detection member is adapted to detect the abutment of the bearing upon the bung and to stop the movement of the first piston rod member. In particular, the detection member may be adapted to detect the abutment of the bearing upon the bung and to stop the movement of the first piston rod member in the operation of adjusting the length of the piston rod.

In particular, the drive mechanism may be the drive mechanism disclosed above such that every structural and functional feature disclosed with respect to that drive mechanism may also be present in the assembly.

In particular, an abutment of the bearing upon the bung may correspond to an increased torque necessary to rotate the adjustment member relative to the second piston rod member. The detection member may detect this increase in the torque and may then stop the movement of the first piston rod member by stopping the rotation of the adjustment member. The detection member may comprise a torque sensor or a slip clutch for this purpose.

Another aspect of the present invention relates to a method for assembling the drug delivery device. The method comprises the steps of:

providing a first piston rod member, a second piston rod member and an adjustment member,
  arranging the adjustment member at least partially inside the second piston rod member,
  operating the adjustment member to move the first piston rod member with respect to the second piston rod member, and
  coupling the first piston rod member with the second piston rod member such that movement between the first piston rod member and the second piston rod member is prevented.

In particular, the method may be used to assemble a drug delivery device comprising the drive mechanism as disclosed above. Accordingly, every structural and functional feature disclosed with respect to that drive mechanism may also be present in the method.

Further, the step of coupling the first piston rod member with the second piston rod member may comprise the sub-step of moving the adjustment member into the second piston rod member such that it is arranged inside the second piston rod member to a greater extent than in the first state of the drive mechanism. The adjustment member may be moved into the second piston rod member such that it is arranged completely inside the second piston rod member.

By moving the adjustment member into the second piston rod member, any unintentional misalignment or any other accidental manipulation of the drive mechanism is prevented as the adjustment member may not be moved accidentally anymore. Thereby the usability and safety of the drug delivery device is increased.

The method may further comprise the step of providing a cartridge comprising a bung. The movement of the first piston rod member in a distal direction may be stopped when the first piston rod member abuts the bung.

Preferably, the first piston rod member, the second piston rod member and the adjustment member are inserted into a body of the drug delivery device before the first piston rod member is moved towards the bung.

The drug delivery device may further comprise a spring member, in particular a back off spring as disclosed above. A force may be applied on the spring member during the movement of the first piston rod member in the distal direction and after the coupling of the first and the second piston rod member to each other, the spring member may be released whereby the piston rod is moved in a proximal direction by a predefined distance. The force on the spring member may be applied by the drive member.

The term "medicinal product", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta'decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group-Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

In the following, the disclosed devices and methods are described in further detail with reference to the drawings, wherein FIG. 1 shows a cross-sectional view of a drug delivery device, FIG. 2 shows a cross-sectional view of the drug delivery device shown in FIG. 1 in a plane perpendicular to a longitudinal axis of a drive mechanism, FIG. 3 shows another cross-sectional view of a part of the drug delivery device of FIG. 1, rotated by 90° compared to the view of FIG. 1.

Figure 1:
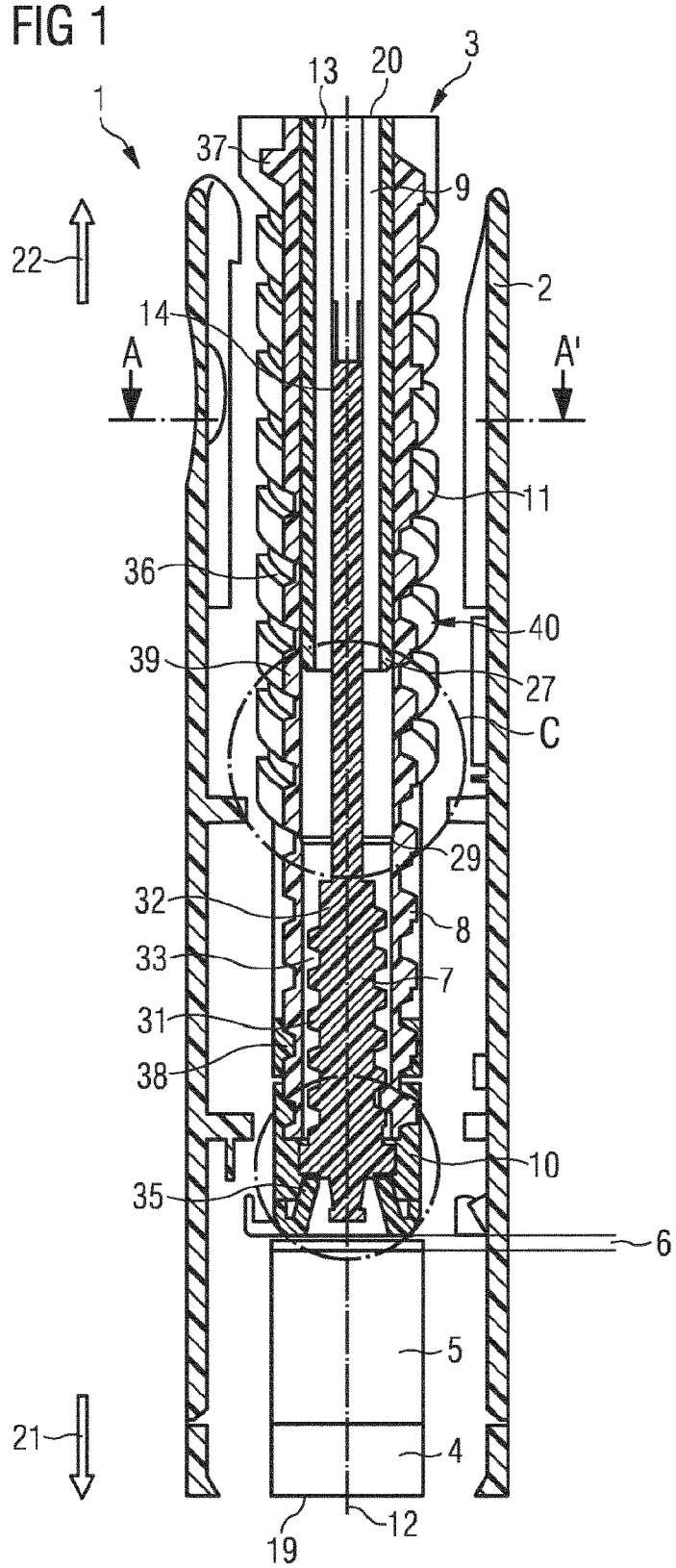
Figure 4:
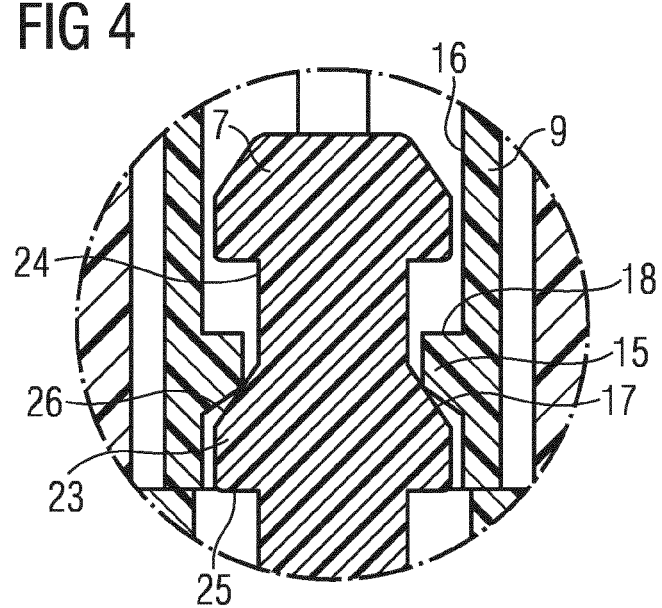
FIG. 4 shows an enlarged view of a part of the drug delivery device shown in FIG. 3.
Figure 5:
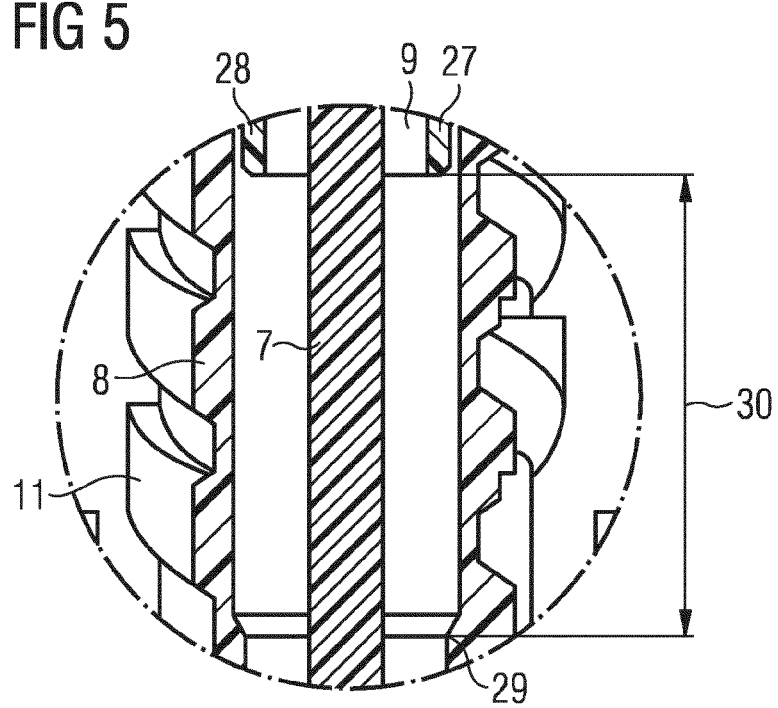
FIG. 5 shows an enlarged view of a part of the drive mechanism shown in FIG. 1.
Figure 6:
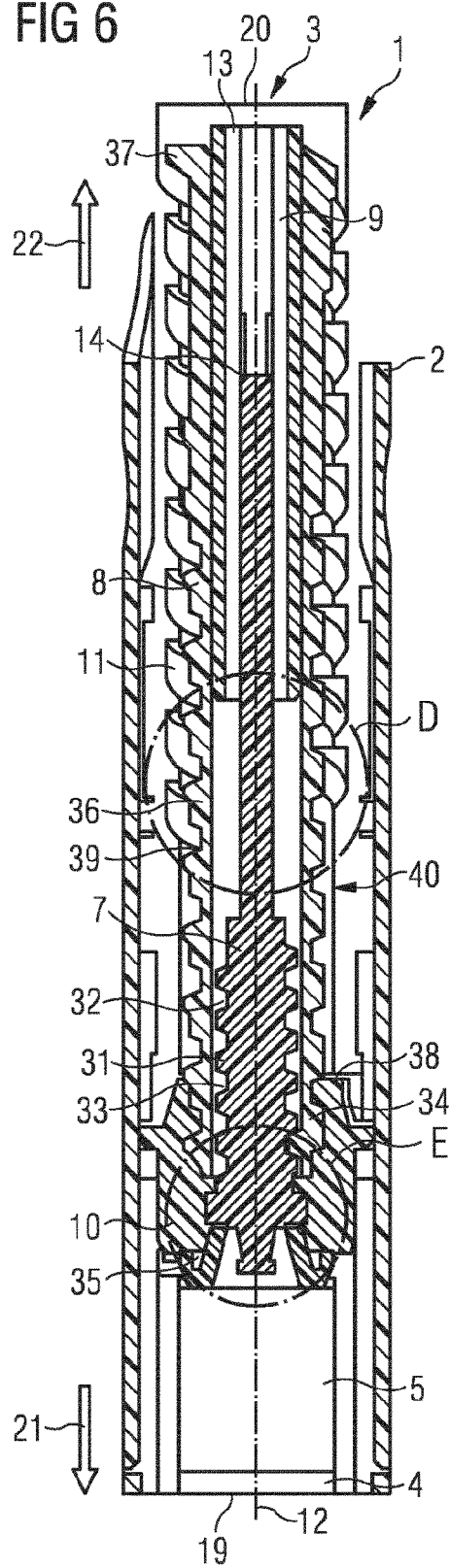
Figure 7:
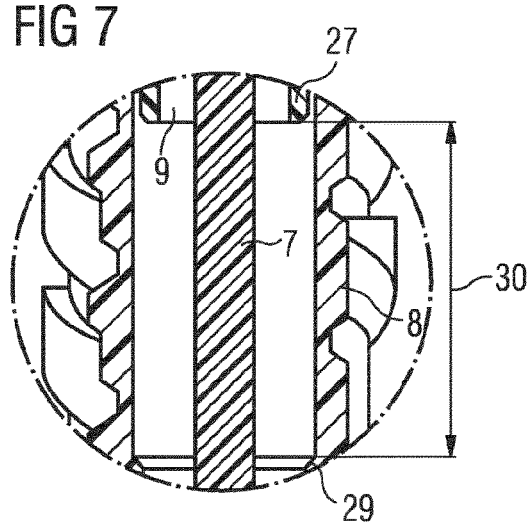
Figure 8:
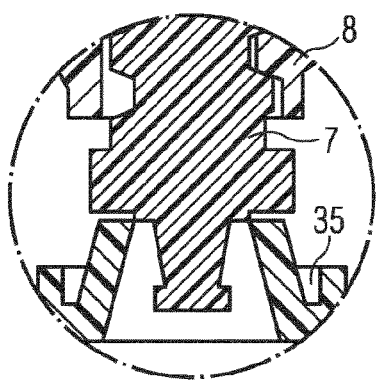
Figure 9:
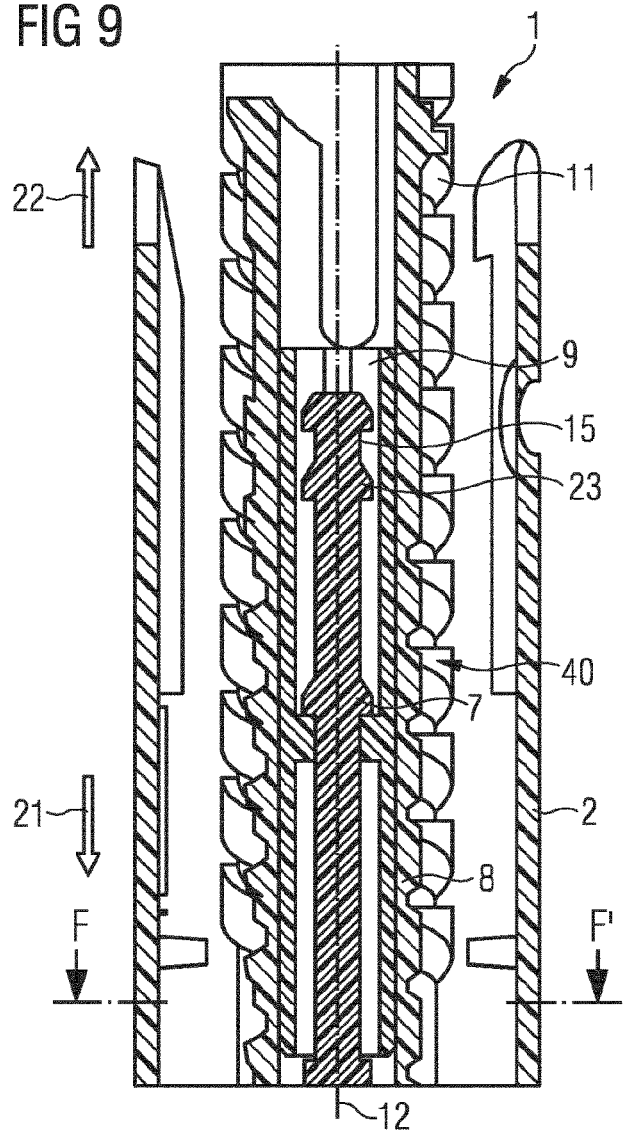
Figure 10:
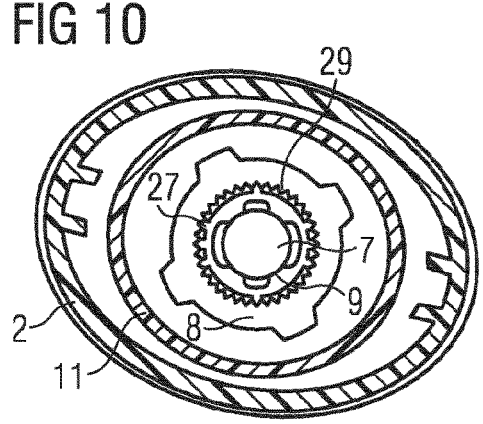

FIG. 6 shows the drug delivery device of FIG. 1 wherein an operation of adjusting a length of a piston rod has been started, FIG. 7 shows an enlarged view of a part of the drive mechanism shown in FIG. 6, FIG. 8 shows an enlarged view of another part of the drive mechanism shown in FIG. 6, FIG. 9 shows the drug delivery device of FIGS. 1 to 8 after the length of the piston rod has been adjusted, and FIG. 10 shows a cross-sectional view of the drug delivery device shown in FIG. 9 in a plane perpendicular to a longitudinal axis of the drive mechanism.

FIG. 1 shows a cross-sectional view of a drug delivery device 1. The drug delivery device 1 shown in FIG. 1 is an injection device. In particular, the drug delivery device 1 is a pen-type injection device.

Moreover, the drug delivery device 1 is a fixed dose device. The drug delivery device 1 is a disposable device.

The drug delivery device 1 comprises a body 2, a drive mechanism 3 and a cartridge 4. The drive mechanism 3 and the cartridge 4 are each arranged at least partially inside the body 2. The cartridge 4 comprises a bung 5. By a movement of the bung 5 in a direction towards an outlet of the cartridge 4, a medicament may be expelled from the cartridge 4.

The drug delivery device 1 comprises a distal end 19 and a proximal end 20.

Figure 2:
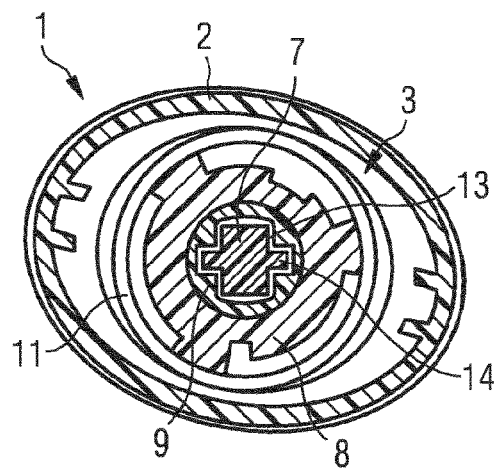

FIG. 2 shows a cross-sectional view of the drug delivery device 1 shown in FIG. 1 in a plane perpendicular to a longitudinal axis of the drive mechanism. In particular, the cross-sectional view of FIG. 2 is taken along a plane AA' as indicated in FIG. 1.

The drive mechanism 3 comprises a first piston rod member 7, a second piston rod member 8 and an adjustment member 9.

Moreover, the drive assembly comprises a nut 10 and a drive member 11.

In particular, the drive member 11, the nut 10, the adjustment member 9, the first piston rod member 7 and the second piston rod member 8 may correspond structurally and functionally to the components of the dosing and drive mechanism disclosed by WO 2008/058665 A1.

The first and the second piston rod member 7, 8 are configured to be fixed to each other. When the first and the second piston rod member 7, 8 are fixed to each other, they form a fixed-length piston rod 40.

The adjustment member 9, the first piston rod member 7 and the second piston rod member 8 are arranged coaxially to a longitudinal axis 12 of the drive mechanism 3.

The adjustment member 9 is arranged at least partially inside the second piston rod member 8. In particular, the second piston rod member 8 comprises an opening which extends through the second piston rod member 8 in a longitudinal direction. The opening has a circular cross-section. The adjustment member 9 has a diameter which is smaller than the diameter of the opening defined in the second piston rod member 8. In particular, the adjustment member 9 is arranged at least partially inside the opening extending through the second piston rod member 8.

Further, the adjustment member 9 also comprises an opening which extends through the adjustment member 9 in a longitudinal direction. The first piston rod member 7 is arranged at least partially inside the adjustment member 9. In particular, the first piston rod member 7 is arranged at least partially inside the opening defined by the adjustment member 9. Thereby, the first piston rod member 7 is also arranged at least partially inside the second piston rod member 8.

The adjustment member 9 comprises a first connection member 13. Further, the first piston rod member 7 comprises a second connection member 14. The first and the second connection members 13, 14 are configured such that a relative rotational movement of the adjustment member 9 and the first piston rod member 7 is prevented when the first and the second connection members 13, 14 are engaged. Further, the first and the second connection members 13, 14 are configured such that a relative translational movement of the adjustment member 9 and the first piston rod member 7 is permitted when the first and the second connection member 13, 14 are engaged. In particular, the first connection member 13 is adapted to slide along the second connection member 14 in a translational direction.

However, as discussed in detail later on, the translational movement of the adjustment member 9 relative to the first piston rod member 7 may be permitted only in one direction, e.g. in a distal direction 21. The translational movement of the adjustment member 9 relative to the first piston rod member 7 may be prevented in the respective other direction, e.g. in a proximal direction 22.

Further, as discussed in detail later on, after the length of the piston rod 40 has been adjusted, the relative translational movement of the adjustment member 9 and the first piston rod member 7 may be prevented.

The first connection member 13 of the adjustment member 9 comprises the opening defined in the adjustment member 9 wherein this opening has a non-circular shape when viewed in a cross-sectional view in a plane perpendicular to the longitudinal axis of the drive mechanism 3. In particular, the opening defined in the adjustment member 9 is cross-shaped when viewed in a cross-sectional view in a plane perpendicular to the longitudinal axis of the drive mechanism 3.

Further, the second connection member 14 of the first piston rod member 7 comprises a part of the first piston rod member 7 having a non-circular cross-section. The non-circular cross-section part of the first piston rod member 7 is arranged inside the non-circular opening of the adjustment member 9. In particular, the part of first piston rod member 7 has a cross-shaped cross-section corresponding to the cross-shaped opening defined in the adjustment member 9.

A relative rotational movement of the adjustment member 9 and the first piston rod member 7 is prevented by the non-circular cross-section part of the first piston rod member 7 being arranged inside the non-circular opening defined in the adjustment member 9.

Figure 3:
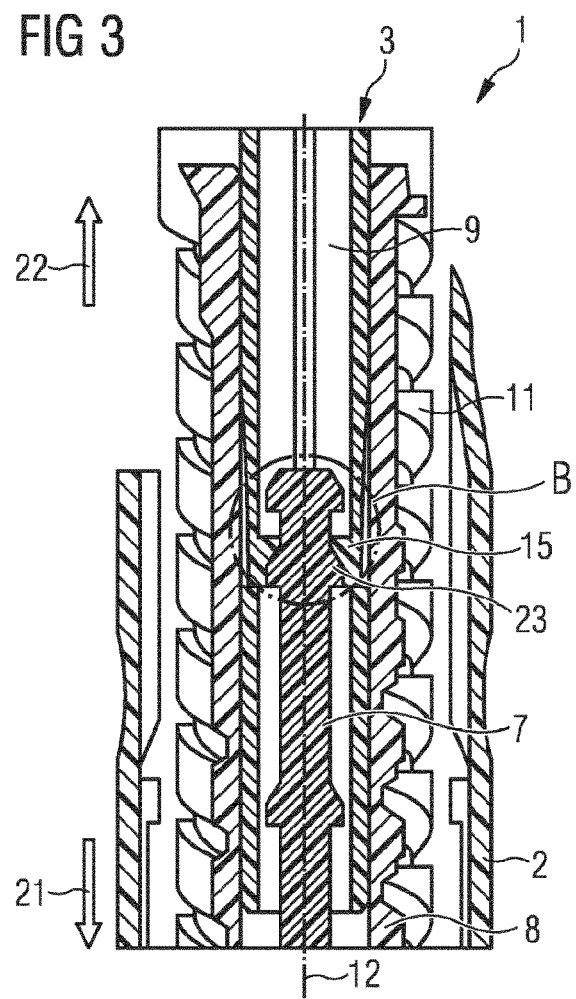

FIG. 3 shows another cross-sectional view of a part of the drug delivery device 1. Compared to the cross-sectional view of FIG. 1, the cutting plane has been rotated by 90° around the longitudinal axis 12 of the drive mechanism 3.

Moreover, FIG. 4 shows an enlarged view of a part of the drug delivery device 1 shown in FIG. 3. In particular, FIG. 4 shows an enlarged view of the area marked by circle B in FIG. 3.

It can be seen from FIGS. 3 and 4 that the adjustment member 9 comprises protrusions 15 at its inner surface 16 extending into the opening defined in the adjustment member 9. In particular, the protrusions 15 are arranged on a flexible arm which is flexible to move in a radial direction towards or away from the longitudinal axis 12 of the drive mechanism 3 by a small distance.

The protrusions 15 extend in a radial direction towards the longitudinal axis 12 of the drive mechanism 3. Each protrusion 15 has a distal face 17 and a proximal face 18. The distal face 17 is defined as the face facing towards a distal end 19 of the drive mechanism 3. Correspondingly, the proximal face 18 is defined as the face facing towards a proximal end 20 of the drive mechanism 3.

The distal faces 17 of the protrusions 15 of the adjustment member 9 are tapered. In particular, the distal faces 17 and the inner surface 16 of the adjustment member 9 include an obtuse angle. Further, the proximal faces 18 of the protrusions 15 of the adjustment member 9 are roughly perpendicular to the longitudinal axis 12 of the drive mechanism 3. Accordingly, the proximal faces 18 and the inner surface 16 of the adjustment member 9 include an angle that is roughly perpendicular.

Moreover, the first piston rod member 7 has protrusions 23 on its outer surface 24 extending in a radial direction away from the longitudinal axis 12 of the drive mechanism 3. When the first piston rod member 7 is arranged inside the adjustment member 9, the protrusions 23 of the first piston rod member 7 may abut the protrusions 15 of the adjustment member 9.

Each of the protrusions 23 of the first piston rod member 7 has a distal face 25 and a proximal face 26. The proximal faces 26 of the protrusions 23 of the first piston rod member 7 are tapered. In particular, the proximal faces 26 and the outer surface 24 of the first piston rod member 7 include an obtuse angle. Further, the distal faces 25 of the protrusions 23 of the first piston rod member 7 are roughly perpendicular to the longitudinal axis 12 of the drive mechanism 3. Accordingly, the distal faces 25 and the outer surface 24 of the first piston rod member 7 include an angle that is roughly perpendicular.

Due to the shaping of the protrusions 15, 23 of the first piston rod member 7 and of the adjustment member 9, a relative translational movement wherein the adjustment member 9 is moved in a distal direction 21 relative to the first piston rod member 7 is permitted as, due to the tapering, the protrusions 15 of the adjustment member 9 may slide over the protrusions 23 of the first piston rod member 7 in the distal direction 21. However, a translational movement of the adjustment member 9 in the proximal direction 22 relative to the first piston rod member 7 is prevented by an abutment of the proximal faces 18 of the protrusions 15 of the adjustment member 9 and the distal faces 25 of the protrusions 23 of the first piston rod member 7.

Further, FIG. 5 shows an enlarged view of a part of the drive mechanism 3 shown in FIG. 1. In particular, the part shown in FIG. 5 is marked in FIG. 1 by the circle C.

It is shown in FIG. 5 that the adjustment member 9 comprises a third connection member 27. The third connection member 27 is arranged at an outer surface 28 of the adjustment member 9. The third connection member 27 comprises splined elements.

The second piston rod member 8 comprises a fourth connection member 29. The fourth connection member 29 is arranged in a distal end part of the second piston rod member 8. The fourth connection member 29 is adapted to be connected with the third connection member 27 of the adjustment member 9. The fourth connection member 29 is arranged at an inner surface 30 of the second piston rod member 8 facing towards the longitudinal axis 12 of the drive mechanism 3. The fourth connection member 29 comprises splined elements.

The third connection member 27 of the adjustment member 9 and the fourth connection member 29 of the second piston rod member 8 are configured such that a relative rotational movement between the adjustment member 9 and the second piston rod member 8 is prevented when the third and the fourth connection member 27, 29 are engaged to each other. Further, the third connection member 27 and the fourth connection member 29 are configured such that a relative translational movement between the adjustment member 9 and the second piston rod member 8 is permitted when the third connection member 27 is connected to the fourth connection member 29.

As discussed in detail later on, in a final state of the assembly of the drug delivery device, the relative translational movement between the adjustment member 9 and the second piston rod member 8 may be prevented.

Furthermore, the first piston rod member 7 comprises a fifth connection member 31 arranged at its outer surface 32. The second piston rod member 8 comprises a sixth connection member 33 arranged at its inner surface 34. The fifth connection member 31 and the sixth connection member 33 are adapted to permit a concurrent relative rotational and translational movement of the first and the second piston rod member 7, 8 when the fifth connection member 31 and the sixth connection member 33 are connected to each other. However, the fifth and the sixth connection member 31, 33 are configured to prevent an exclusive rotational movement and an exclusive translational movement of the first and the second piston rod member 7, 8 relative to each other when the fifth and the sixth connection member 31, 33 are engaged to each other.

In particular, the fifth and the sixth connection member 31, 33 are adapted such that the first and the second piston rod member 7, 8 are threadedly engaged to each other, as shown in FIG. 1. Accordingly, the fifth connection member 31 comprises a helical thread and the sixth connection member 33 comprises a helical thread, wherein said two helical threads are engageable with each other and allow the first piston rod member 7 to be screwed into the second piston rod member 8 or out of the second piston rod member 8.

Further, the first piston rod member 7 comprises a bearing 35 arranged at its distal end. The bearing 35 is configured to abut the bung 5 in the cartridge 4. Furthermore, the bearing 35 of the first piston rod member 7 is adapted to provide a force on the bung 5 such that the bung 5 is moved in a distal direction 21 and a medicament is expelled from the cartridge 4.

Moreover, the drive mechanism 3 comprises the drive member 11 and the nut 10. The drive member 11 comprises a drive sleeve.

The adjustment member 9, the first piston rod member 7 and the second piston rod member 8 are arranged at least partially inside the drive member 11. The drive member 11 is adapted to be moved in an axial direction. In particular, the drive member 11 can be moved in the distal direction 21 and in the proximal direction 22. However, the drive member 11 is connected to the body 2 such that a rotational movement of the drive member 11 relative to the body 2 is prevented.

Further, the second piston rod member 8 comprises a first thread 39 at its distal end and a second thread 37 at its proximal end. The first and the second thread 39, 37 are arranged at the outer surface of the second piston rod member 8.

The first thread 39 comprises helical sections and flat sections. The helical sections and the flat sections are arranged alternatingly to each other on the first thread 39. Accordingly, the first thread 39 defines a path of alternating helical and flat sections. The flat sections act as non-return features.

The second thread 37 comprises a series of part threads, rather than a complete thread. The part threads are formed on flexible arms of the second piston rod member 8.

The first thread 39 and the second thread 37 of the second piston rod member 8 are oppositely disposed.

The nut 10 is arranged at the distal end of the drive member 11. In particular, the nut 10 is provided with a threaded circular opening. In the shown embodiment, the threaded circular opening comprises a series of part threads rather than a complete thread. Additionally, the nut 10 comprises non-return features (not shown), e.g. flat sections in the part threads.

Further, the second piston rod member 8 extends through the nut 10. The second piston rod member 8 is threadedly engaged with the nut 10 by an engagement of the first thread 39 of the second piston rod member 8 and the threaded circular opening of the nut 10. When the second piston rod member 8 is moved relative to the nut 10, the relative movement is constrained by the path defined by the first thread 39.

Moreover, the nut 10 is rotationally and translationally fixed to the body 2.

The drive member 11 comprises a thread 36 at its inner surface.

The drive member 11 and the second piston rod member 8 are configured such that the thread 36 of the drive member 11 and the second thread 37 of the second piston rod member 8 engage to each other when the drive member 11 is moved in the distal direction 21. Due to the threaded engagement of the drive member 11 and the second piston rod member 8, the second piston rod member 8 carries out a rotational movement, when the drive member 11 is moved in the distal direction 21.

Further, the drive member 11 is configured such that the drive member 11 and the second piston rod member 8 disengage from each other, when the drive member 11 moves in the proximal direction 21. Accordingly, the second piston rod member 8 does not move, when the drive member 11 moves in the proximal direction 21.

In particular, the first thread 39 of the second piston rod member 8 is provided with a plurality of non-return features, e. g. flat sections, (not shown) that cooperate with the non-return features of the threaded circular opening of the nut 10 to prevent a movement of the second piston rod member 8 in the proximal direction 21 when the drive member 11 moves in the proximal direction 21.

Additionally, the second piston rod member 8 is provided with a plurality of non-return features, e.g. splined sections, (not shown) that cooperate with a corresponding non-return feature of the drive member to prevent a movement of the second piston rod member 8 in the proximal direction 21 when the drive member 11 moves in the proximal direction 21.

Moreover, the drive mechanism 3 comprises a spring member 38. The spring member 38 is arranged at the proximal end of the nut 10. The spring member 38 is adapted to move the second piston rod member 8 in the proximal direction 22. In particular, when the spring member 38 is tensed and then allowed to release, this results in a movement of the second piston rod member 8 in the proximal direction 22. Each element that is translationally fixed to the second piston rod member 8 follows this movement.

The spring member 38 may be tensed by the drive member 11 moving in a distal direction and thereby applying a force on the spring member 38. Once the force applied by the drive member 11 is released, the spring member 38 is allowed to relax. Thereby, the spring member 38 exerts a force on the drive member 11 in a proximal direction, resulting in a small movement of the drive member 11 in the proximal direction. This movement also causes a small proximal movement of the second piston rod member 8.

Furthermore, the adjustment member 9 comprises a contact area (not shown) which is adapted for engagement with a tool. For example, a gripping tool may engage to the outer surface of the adjustment member 9 wherein the outer surface extends out of the second piston rod member 8 at its proximal end. The gripping tool may rotate the adjustment member 9 during assembly.

FIGS. 1 to 5 show the drug delivery device 1 in a first state. The first state of the drug delivery device 1 corresponds to the drive mechanism 3 being in its first state. The first state of the drive mechanism 3 corresponds to a stage in the assembly process wherein, due to manufacturing tolerances, the drive mechanism 3 and the cartridge 4 have not yet been aligned to each other such that the distance 6 between the drive mechanism 3 and the bung 5 is not well-defined. In particular, the distance 6 may vary from one drug delivery device 1 to another at this stage of the assembly process.

The first state may be a pre-assembled state. In other words, the manufacturing process has not been completed in the first state. In particular, an adjustment of the length of the piston rod 40 has not been carried out.

In the first state, the first connection member 13 of the adjustment member 9 is connected to the second connection member 14 of the first piston rod member 7. Accordingly, in the first state, the first piston rod member 7 has to follow a rotational movement of the adjustment member 9.

Further, in the first state of the drive mechanism 3, the third connection member 27 of the adjustment member 9 is not engaged to the fourth connection member 29 of the second piston rod member 8. Instead, the third and the fourth connection members 27, 29 are arranged at a distance 30 from each other. Accordingly, in the first state, the third and the fourth connection members 27, 29 do not prevent any relative movement of the adjustment member 9 and the second piston rod member 8.

One of the operations carried out during an assembly process of the drug delivery device 1 is an adjustment of the length of the piston rod. This operation allows adjusting for manufacturing tolerances and other mechanical tolerances.

A first step of the operation of adjusting the length of the piston rod 40 is moving the drive member 11 in a distal direction. In particular, the drive member 11 is held in the distal position during the whole operation of adjusting the length of the piston rod 40.

When the drive member 11 moves in the distal direction, it abuts the nut 10 and exerts a force on the spring member 38 arranged at the proximal end of the nut 10, thereby the spring member 38 is tensed.

However, this first step of the operation of adjusting the length of the piston rod 40 is optional. It does not have to be carried out to adjust the length of the piston rod 40.

FIGS. 6, 7 and 8 show the drug delivery device 1 during a further step of the operation of adjusting the length of the piston rod 40.

FIG. 7 shows an enlarged view of a part of the drive mechanism 3 shown in FIG. 6. In particular, the part shown in FIG. 7 is marked in FIG. 6 by the circle D.

FIG. 8 shows an enlarged view of a part of the drive mechanism 3 shown in FIG. 6. In particular, the part shown in FIG. 8 is marked in FIG. 6 by the circle E.

In this further step, the adjustment member 9 is rotated about the longitudinal axis 12.

Due to the connection of the first and the second connection member 13, 14, the first piston rod member 7 is rotationally fixed to the adjustment member 9 such that the first piston rod member 7 follows the rotational movement of the adjustment member 9.

Further, in the first state, the third and the fourth connection member 27, 29 are not connected to each other. This is not altered in the further step of the operation of adjusting the length of the piston rod 40 shown in FIGS. 6 to 8. Accordingly, a relative rotational and axial movement of the adjustment member 9 relative to the second piston rod member 8 is permitted. In particular, a movement of the adjustment member 9 is not transferred into a movement of the second piston rod member 8.

Accordingly, the first piston rod member 7 following the rotational movement of the adjustment member 9 is rotated relative to the second piston rod member 8.

Furthermore, the fifth and the sixth connection member 31, 33 of the first and the second piston rod member 7, 8 are connected to each other, thereby allowing only a concurrent and axial movement relative to the first and the second piston rod member 7, 8. Accordingly, the rotational movement of the first piston rod member 7 relative to the second piston rod member 8 also triggers a movement of the first piston rod member 7 in a distal direction relative to the second piston rod member 8.

Due to the movement of the first piston rod member 7 in the distal direction, the distance 30 between the third connection member 27 of the adjustment member 9 and the fourth connection member 29 of the second piston rod member 8 is reduced.

Due to the movement of the first piston rod member 7 in the distal direction, the bearing 35 of the first piston rod member 7 is moved closer to the bung 5 of the cartridge 4.

In particular, FIGS. 6 to 8 show the drug delivery device 1 in a situation wherein the first piston rod member 7 is now in abutment with the bung 5. In particular, the bearing 35 of the first piston rod member 7 abuts the bung 5.

Once the bearing 35 abuts the bung 5, the torque required to rotate the adjustment member 9 increases.

For the adjustment of the length of the piston rod 40, a detection member is used to detect the abutment of the bearing 35 on the bung 5 and to stop the movement of the first piston rod member 7 in the distal direction 21 in case of abutment. In particular, the detection member may detect the increase in the torque required to rotate the adjustment member 9. The detection member may comprise a torque sensor or a slip clutch for this purpose. For example, once the bearing 35 contacts the bung 5, the slip clutch may slip due to the increased torque and, thereby, the rotation of the adjustment member 9 is stopped. This also stops the movement of the first piston rod member 7.

A last step of the adjustment of the length of the piston rod 40 is carried out when an abutment of the bearing 35 and the bung 5 has been detected and when the rotation of the adjustment member 9 has been stopped.

In the last step of the adjustment of the length of the piston rod 40, the adjustment member 9 is pushed inward into the second piston rod member 8. The protrusions 15 on the inner surface 16 of the adjustment member 9 slide over the corresponding protrusions 23 on the outer surface 24 of the first piston rod member 7. Accordingly, the adjustment member 9 is moved in the distal direction 21 relative to the first piston rod member 7 and relative to the second piston rod member 8.

During this translational movement, the third connection member 27 of the adjustment member 9 and the fourth connection member 29 of the second piston rod member 8 are connected to each other. Thereby, a rotational movement of the adjustment member 9 relative to the second piston rod member 8 is prevented.

Accordingly, the adjustment member 9 is prevented from a rotational movement relative to the first piston rod member 7 due to the connection of the first and the second connection member 13, 14 and, further, due to the connection of the third and the fourth connection member 27, 29, the adjustment member 9 is prevented from a rotational movement relative to the second piston rod member 8. Accordingly, as the first and the second connection member 13, 14 are connected to each other and the third and the fourth connection member 27, 29 are connected to each other, a relative rotational movement of the first and the second piston rod member 7, 8 is also prevented.

Moreover, due to the engagement of the fifth and the sixth connection member 31, 33, the first and the second piston rod member 7, 8 are only allowed to carry out concurrent rotational and translational movements. As rotational movements are no longer possible, the first and the second piston rod member 7, 8 are thereby also translationally fixed to each other after the last step has been carried out.

Therefore, the first and the second piston rod member 7, 8 define the piston rod 40 of a fixed length. In particular, after the last step of the adjustment of the length of the piston rod 40 has been completed, the length of the piston rod 40 cannot be altered such that the drug delivery device 1 is operated with the piston rod 40 of a fixed length.

In case the optional first step of moving the drive member 11 in the distal direction 21 and of holding the drive member 11 in its distal position is carried out, in the last step of the adjustment of the length of the piston rod 40 comprises the sub-step of releasing the drive member 11. Accordingly, the drive member 11 is not held in its distal position anymore. Then, the drive member 11 does not apply a force on the spring member 38 anymore and the spring member 38 is allowed to relax.

When the spring member 38 relaxes, it moves the drive member 11 in the proximal direction 22. Moreover, when the spring member 38 relaxes, this also results in a movement of the second piston rod member 8 in the proximal direction 22. Thereby, the complete fixed length piston rod 40 is moved in the proximal direction 22.

Thereby, the fixed length piston rod 40 is moved by a predefined distance relative to the bung 5. This distance is defined by the compression length of the spring member 38.

The spring member 38 thereby ensures that the piston rod 40 is not in permanent abutment with the bung 5. Instead, after the adjustment of the length of the piston rod 40 is completed, the piston rod 40 is withdrawn from the bung 5 by the predefined distance such that no force is exerted on the bung 5. Accordingly, it is prevented that fluid drips out of the cartridge when a needle is attached to the cartridge.

As the piston rod 40 now has a predefined distance to the bung 5, a priming step is no longer necessary.

However, it is not necessary for the adjustment of the length of the piston rod 40 that the drive member 11 is pushed in the distal direction 21 during assembly.

FIG. 9 shows the drug delivery device 1 after the final step of the adjustment of the length of the piston rod 40. FIG. 9 shows a cross-sectional view of a part of the drive mechanism 3. Furthermore, FIG. 10 shows a cross-sectional view taken along the plane FF' in FIG. 9 in the second state after the adjustment of the length of the piston rod 40 is completed.

Moreover, FIGS. 9 and 10 show the drug delivery device 1 in a second state. The second state of the drug delivery device 1 corresponds to a second state of the drive mechanism 3.

The second state of the drive mechanism 3 is defined by the first and the second piston rod member 7, 8 being fixed to each other to define the fixed length piston rod 40. Further, in the second state of the drive mechanism 3, the drug delivery device 1 is ready to dispense a medicament from the cartridge 4. In particular, the drug delivery device 1 is ready to be operated by a user.

In the first state, the distance 6 between the drive mechanism 3 and the cartridge 4, or respectively between the bearing 35 and the bung 5 of the cartridge 4, is not precisely defined. In particular, due to manufacturing tolerances, this distance 6 varies from one drug delivery device 1 to another. However, when the drive mechanism 3 is in the second state, this distance 6 has been adjusted such that the bearing 35 either abuts the bung 5 or has a predefined distance to the bung 5. Accordingly, it will not be necessary for a user to carry out a priming step before the first operation of the drug delivery device 1. The second state is a state wherein the adjustment of the length of the piston rod 40 has been completed.

Furthermore, after the adjustment of the length of the piston rod 40 is completed, other assembling steps may be carried out. For example, a button may be attached to the drive member 11. The button may close the body 2. For dose setting, the button may be pulled in the proximal direction and for dose dispensing, the button may be pushed in the distal direction.

REFERENCE NUMERALS 1 drug delivery device
2 body
3 drive mechanism
4 cartridge
5 bung
6 distance between drive mechanism and cartridge
7 first piston rod member
8 second piston rod member 9 adjustment member
10 nut
11 drive member
12 longitudinal axis
13 first connection member
14 second connection member
15 protrusion
16 inner surface of the adjustment member
17 distal face
18 proximal face
19 distal end
20 proximal end
21 distal direction
22 proximal direction
23 protrusion
24 outer surface of the first piston rod member
25 distal face
26 proximal face
27 third connection member
28 outer surface of the adjustment member
29 fourth connection member
30 distance between the third and the fourth connection member
31 fifth connection member
32 outer surface of the first piston rod member
33 sixth connection member
34 inner surface of the second piston rod member
35 bearing
36 thread
37 second thread
38 spring member
39 first thread
40 piston rod

The invention claimed is:

1. A drive mechanism for a drug delivery device, the drive mechanism comprising:
   a piston rod comprising a first piston rod member and a second piston rod member; and
   an adjustment member, wherein the drive mechanism has a first state in which the first and the second piston rod member are moveable with respect to each other by operating the adjustment member, thereby adjusting a length of the piston rod, and
   wherein the adjustment member is arranged at least partially inside the second piston rod member and wherein the adjustment member is configured to be moved completely into the second piston rod member.

2. The drive mechanism according to claim 1, wherein the drive mechanism has a second state in which the first piston rod member is fixed to the second piston rod member to define a fixed length of the piston rod.

3. The drive mechanism according to claim 1,
   wherein the adjustment member comprises a first connection member,
   wherein the first piston rod member comprises a second connection member, and wherein the first connection member and the second connection member are configured to prevent a rotational movement of the adjustment member and the first piston rod member relative to each other and to permit a relative translational movement of the adjustment member and the first piston rod member when the first connection member and the second connection member are connected to each other.

4. The drive mechanism according to claim 1,
   wherein the adjustment member comprises a third connection member, and
   wherein the second piston rod member comprises a fourth connection member, and wherein the third connection member and the fourth connection member are configured to prevent a rotational movement of the adjustment member and the second piston rod member relative to each other and to permit a relative axial movement of the adjustment member and the second piston rod member when the third connection member and the fourth connection member are connected to each other.

5. The drive mechanism according to claim 4, wherein the first piston rod member is moveable relative to the second piston rod member when the third connection member and the fourth connection member are not connected to each other.

6. The drive mechanism according to claim 4, wherein a relative movement of the first piston rod member and the second piston rod member is prevented when the third connection member and the fourth connection member are connected to each other.

7. The drive mechanism according to claim 1, wherein the first piston rod member comprises a fifth connection member and the second piston rod member comprises a sixth connection member, and
   wherein when the fifth connection member and the sixth connection member are connected to each other such that a movement between the first and the second piston rod member is restricted to a concurrent rotational and translational movement.

8. The drive mechanism according to claim 1,
   wherein the first piston rod member is arranged at least partly inside the second piston rod member, and
   wherein the first piston rod member is arranged at least partly inside the adjustment member.

9. The drive mechanism according to claim 1, wherein the adjustment member is arranged such that a rotational movement of the adjustment member relative to the second piston rod member advances the first piston rod member relative to the second piston rod member.

10. The drive mechanism according to claim 1, further comprising a spring member that is adapted to move the piston rod after adjustment of the length of the piston rod in a proximal direction.

11. A method for assembling a drug delivery device, the method comprising:
    providing a first piston rod member, a second piston rod member and an adjustment member;
    arranging the adjustment member at least partly inside the second piston rod member;
    operating the adjustment member to move the first piston rod member with respect to the second piston rod member; and
    coupling the first piston rod member with the second piston rod member such that movement between the first piston rod member and the second piston rod member is prevented,
    wherein the drive mechanism has a first state in which the first and the second piston rod member are moveable with respect to each other by operating the adjustment member, thereby adjusting a length of the piston rod,
    wherein coupling the first piston rod member with the second piston rod member comprises moving the adjustment member completely into the second piston rod member such that the adjustment member is arranged inside the second piston rod member to a greater extent than in the first state of the drive mechanism.

12. The method of claim 11, further comprising:
providing a cartridge comprising a bung, wherein the movement of the first piston rod member in a distal direction is stopped when the first piston rod member abuts the bung.

13. The method of claim 11,
wherein the drug delivery device further comprises a spring member, and wherein the method comprises:
applying a force on the spring member during the movement of the first piston rod member in the distal direction; and
after coupling the first piston rod member and the second piston rod member to each other, releasing the spring member whereby the piston rod is moved in a proximal direction by a predefined distance.

14. A drive mechanism for a drug delivery device, the drive mechanism comprising:
a piston rod comprising a first piston rod member and a second piston rod member; and
an adjustment member, wherein the drive mechanism has a first state in which the first and the second piston rod member are moveable with respect to each other by operating the adjustment member, thereby adjusting a length of the piston rod,
wherein the adjustment member is arranged at least partially inside the second piston rod member,
wherein the adjustment member comprises a third connection member,
wherein the second piston rod member comprises a fourth connection member, and wherein the third connection member and the fourth connection member are configured to prevent a rotational movement of the adjustment member and the second piston rod member relative to each other and to permit a relative axial movement of the adjustment member and the second piston rod member when the third connection member and the fourth connection member are connected to each other, and
wherein the first piston rod member is moveable relative to the second piston rod member when the third connection member and the fourth connection member are not connected to each other.

15. A drive mechanism for a drug delivery device, the drive mechanism comprising:
a piston rod comprising a first piston rod member and a second piston rod member; and
an adjustment member, wherein the drive mechanism has a first state in which the first and the second piston rod member are moveable with respect to each other by operating the adjustment member, thereby adjusting a length of the piston rod,
wherein the adjustment member is arranged at least partially inside the second piston rod member,
wherein the first piston rod member comprises a fifth connection member and the second piston rod member comprises a sixth connection member, and
wherein when the fifth connection member and the sixth connection member are connected to each other such that a movement between the first and the second piston rod member is restricted to a concurrent rotational and translational movement.

\* \* \* \* \*

UNITED STATES PATENT AND TRADEMARK OFFICE
CERTIFICATE OF CORRECTION

PATENT NO. : 10,293,111 B2
APPLICATION NO. : 14/913153
DATED : May 21, 2019
INVENTOR(S) : Samuel Keir Steel et al.

It is certified that error appears in the above-identified patent and that said Letters Patent is hereby corrected as shown below:

On the Title Page

Item (73), Column 1 (Assignee), Line 1, delete "Sanofi-Anentis Deutschland GMBH," and insert -- Sanofi-Aventis Deutschland GMBH, --

Signed and Sealed this
Ninth Day of July, 2019

Andrei Iancu
*Director of the United States Patent and Trademark Office*